United States Patent
Nowinski et al.

(10) Patent No.: US 8,019,142 B2
(45) Date of Patent: Sep. 13, 2011

(54) SUPERIMPOSING BRAIN ATLAS IMAGES AND BRAIN IMAGES WITH DELINEATION OF INFARCT AND PENUMBRA FOR STROKE DIAGNOSIS

(75) Inventors: Wieslaw L. Nowinski, Singapore (SG); Norman J. Beauchamp, Seattle, WA (US)

(73) Assignee: Agency for Science, Technology and Research, Centros (SG)

( * ) Notice: Subject to any disclaimer, the term of this patent is extended or adjusted under 35 U.S.C. 154(b) by 720 days.

(21) Appl. No.: 12/067,894

(22) PCT Filed: Nov. 21, 2006

(86) PCT No.: PCT/SG2006/000357
§ 371 (c)(1),
(2), (4) Date: Jul. 23, 2008

(87) PCT Pub. No.: WO2007/058632
PCT Pub. Date: May 24, 2007

(65) Prior Publication Data
US 2009/0034812 A1 Feb. 5, 2009

Related U.S. Application Data

(60) Provisional application No. 60/738,071, filed on Nov. 21, 2005.

(51) Int. Cl.
*G06K 9/54* (2006.01)
(52) U.S. Cl. ...................................................... 382/131
(58) Field of Classification Search ................. 378/4, 19, 378/62, 64; 382/128, 130, 131, 132, 284, 382/294
See application file for complete search history.

(56) References Cited

U.S. PATENT DOCUMENTS

| 5,961,454 A | 10/1999 | Kooy et al. |
| 6,792,302 B2 * | 9/2004 | Wintermark et al. .......... 600/407 |
| 7,580,737 B2 * | 8/2009 | Wintermark et al. .......... 600/407 |
| 7,627,078 B2 * | 12/2009 | Hsieh et al. ....................... 378/4 |

(Continued)

FOREIGN PATENT DOCUMENTS
WO WO 02/43003 A1 5/2002
(Continued)

OTHER PUBLICATIONS

Hu et al., "A rapid algorithm for robust and automatic extraction of the midsagittal plane of the human cerebrum from neuroimages based on local symmetry and outlier removal," Neuroimage, (2003) 20:2153-2165.

(Continued)

*Primary Examiner* — Irakli Kiknadze
(74) *Attorney, Agent, or Firm* — Kilpatrick Townsend & Sockton LLP

(57) ABSTRACT

Brain images are processed and analyzed with the aid of a computer for stroke diagnosis or therapeutic decision making, where multiple stroke-related images are superimposed. The superimposed images include brain images that have infarct and penumbra regions, and patient-specific brain atlas images. The infarct and penumbra regions are determined and delineated on the superimposed images. Each patient-specific brain atlas image may be formed by mapping a pre-existing brain atlas to a co-ordinate system in which the brain images are co-registered. A brain atlas may depict brain structures such as anatomy structures, blood supply territories (BST), or cerebral vasculature. The superimposed images may be used to determine any overlap between a particular brain structure and the infarct and penumbra regions.

23 Claims, 12 Drawing Sheets

U.S. PATENT DOCUMENTS

2005/0273001 A1    12/2005    Schmainda et al.
2006/0142983 A1*    6/2006    Sorensen et al. ............... 703/11

FOREIGN PATENT DOCUMENTS

WO    WO 2005/048844 A1    6/2005
WO    WO 2005/096227 A1    10/2005

OTHER PUBLICATIONS

Hu et al., "Fast connected-component labelling in three dimensional binary images based on iterative recursion," Computer Vision and Image Understanding, (2005) 99:414-435.

Hu et al., "Fast, accurate, and automatic extraction of the modified Talairach cortical landmarks from magnetic resonance images," Magn. Reson. Med., (2005) 53:970-6.

Hu et al., "Supervised range-constrained thresholding," IEEE Transactions on Image Processing, (2006) 15(1):228-240.

Lorensen et al., "Marching cubes; a high resolution 3D surface construction algorithm," Computer Graphics (1987) 21(4):163-169.

Nowinski et al., "Analysis of ischemic stroke MR images by means of brain atlases of anatomy and blood supply territories[1]," Technical Report, Acad. Radiol. (2006) 13:1025-1034.

Nowinski et al., "Atlas-assisted MR stroke image interpretation by using anatomical and blood supply territories atlases," Program, 91st Radiological Society of North American Scientific Assembly and Annual Meeting RSNA 2005, Chicago, IL, USA, Nov. 37-Dec. 2, 2005, p. 857.

Nowinski et al., "Multiple brain atlas database and atlas-based neuroimaging system," Computer Aided Surgery, (1997) 2:42-66.

Nowinski et al., "Rapid and automatic calculation of the midsagittal plane in magnetic resonance diffusion and perfusion images[1]," Academic Radiology (2006) 13:652-663.

Nowinski et al., "The cerefy brain atlases, continuous engancement of the electronic Talairach-Tournoux brain atlas," Neruoinformatics (2005) 3:293-300.

Nowinski et al., 3D Image Processing: Techniques and Clinical Applications, "Electronic brain atlases: features and applications," Medical Radiology series, eds. D. Caramella and C. Bartolozzi, Springer, 2002, pp. 79-93.

Nowinski, "Modified Talairach landmarks," Technical Report, Acta Neurochir, (2001)143:1045-1057.

Parsons et al., "Therapeutic impact of MRI in acute stroke," in Magnetic Resonance Imaging in Ischemic Stroke, R. von Kummer and T. Back eds., Springer, Berlin, 2006, pp. 23-40.

Prakash et al., "Rapid and automatic localization of the anterior and posterior commissure point landmarks in MR volumetric neuroimages[1]," Acad. Radiol. (2006) 13:36-54.

* cited by examiner

SUPERIMPOSING BRAIN ATLAS IMAGES AND BRAIN IMAGES WITH DELINEATION OF INFARCT AND PENUMBRA FOR STROKE DIAGNOSIS

FIELD OF THE INVENTION

The present invention relates to presentation, processing and analysis of brain images for stroke diagnosis.

BACKGROUND OF THE INVENTION

Stroke can cause disability and death. Timely treatment of stroke can save lives and reduce damages suffered by the patients. Stroke related diagnosis and treatment planning are made at least in part based on the medical images of the patient, such as computerized tomography (CT) or magnetic resonance (MR) images. Conventionally, these images are visually inspected by a medical personnel for diagnosis and treatment of stroke. Typically, multiple images need to be inspected and analyzed, which include brain images that depicting, respectively, anatomy, angiography, diffusion, perfusion, and the like.

There are some drawbacks associated with the conventional approaches to image-based stroke diagnosis and treatment planning. One problem is that human judgment can vary dependent on several factors such as perception, experience, fatigue, bias, and background noise, and thus can be inconsistent and inaccurate. As the number of images needs to be viewed increases, the difficulty of arriving at a correct diagnosis may also increase. Further, inspecting and analyzing multiple images can be time consuming. It is estimated that during a stroke about 1.9 million nerve cells die each minute and the ischemic brain ages about 3.9 years each hour. In this sense, it is said that "time is brain". Therefore, it is desirable that a proper stroke treatment can be determined and implemented as soon as possible after a stroke has occurred.

SUMMARY OF THE INVENTION

Brain images are processed and analyzed with the aid of a computer for stroke diagnosis or treatment planning, where multiple stroke-related images are superimposed. The superimposed images include brain images that have infarct and penumbra regions, and patient-specific brain atlas images. The infarct and penumbra regions are determined and delineated on the superimposed images. Each patient-specific brain atlas image may be formed by mapping a pre-existing brain atlas to a co-ordinate system in which the brain images are co-registered. A brain atlas may depict brain structures such as anatomy structures, blood supply territories (BST), or cerebral vasculature. The superimposed images may be used to determine any overlap between a particular brain structure and the infarct and penumbra regions.

Thus, such overlaps, and the brain structures that overlap with any of the infarct and penumbra regions, can be conveniently identified and visualized. The degree of overlap between the infarct or penumbra region and any particular brain structure may be assessed, such as calculated or otherwise quantified. For example, a volume of the overlap or a volume ratio between the volume of the overlap and the volume of the brain structure may be calculated. The superimposed images may be processed automatically to quantify diffusion-perfusion mismatch, and quantify the sizes of infarcts relative to the middle cerebral artery (MCA) territory. The superimposed images may also be displayed, optionally with data generated from the superimposed images, to allow a user to conveniently performing stroke analysis. For example, the data may include the identifications of the brain structures that overlap with any of the infarct and penumbra regions, and the corresponding calculated volume ratios. Exemplary embodiments of the present invention can provide rapid, automatic and quantitative assessment based on anatomy, angiography, diffusion, and perfusion scans. The size of the infarct versus that of middle cerebral artery territory and the diffusion-perfusion mismatch can be calculated rapidly, automatically, and quantitatively. An exemplary method according an aspect of the present invention can support the thrombolysis algorithm.

Thus, in accordance with an aspect of the present invention, there is provided a method of analyzing brain images of a patient for stroke diagnosis of the patient. The method comprises capturing a first image of the brain of the patient suitable for determining infarct regions of the brain; capturing a second image of the brain suitable for determining penumbra regions of the brain; determining an infarct region of the brain from the first image; determining a penumbra region of the brain from the second image; co-registering the first and second images to a co-ordinate system; mapping pre-existing brain atlas images to the co-ordinate system to form patient-specific brain atlas images; delineating the infarct region and the penumbra region of the brain on the patient-specific brain atlas images in the co-ordinate system; and superimposing the first and second images, with the patient-specific brain atlas images.

Delineation of the infarct region and the penumbra region on the superimposed images may be modified. A degree of overlap between one of the infarct and penumbra regions and a brain structure depicted in the patient-specific brain atlas images may be determined. The degree of overlap may be determined by calculating a volume of the overlap, or a volume ratio between a volume of the overlap and a volume of the brain structure. An identification of the brain structure and at least one of the volume and the volume ratio may be presented to a user. Brain structures in the patient-specific brain atlas images that overlap with one of the infarct and penumbra regions may be identified. The pre-existing brain atlas images may comprise an anatomy atlas image depicting at least one anatomical structure and a blood supply territory (BST) atlas image depicting blood supply territories. The BST atlas image may depict the MCA. A volume ratio between the infarct region and the MCA may be calculated. A ratio of the volume of the infarct region and the volume of an overlap between the infarct region and the MCA may be calculated. The first image may comprise a diffusion image. The diffusion image may be a diffusion weighted imaging (DWI) image.

The infarct region may be determined by: generating an apparent diffusion coefficient (ADC) map image from at least two diffusion images; determining a present infarct region from one of the diffusion images; determining a prior infarct region from one of the diffusion images and the ADC map image; and combining the present and prior infarct regions to form the infarct region.

The second image may comprise a perfusion image. The perfusion image may be a perfusion-weighted imaging (PWI) image.

The penumbra region may be determined by: generating at least one perfusion map image from the perfusion image, the at least one perfusion map image selected from mean transit time (MTT), cerebral blood flow (CBF), cerebral blood volume (CBV), time to peak (TTP), and peak-height (PKHT) map images; superimposing the perfusion image and the at least one perfusion map image; and determining an apparent penumbra region from the superimposed perfusion image and the at least one perfusion map image.

The penumbra region may be determined by excluding from the apparent penumbra region any overlap with the infract region to form the penumbra region.

At least one additional image of the brain may be captured and superimposed with the first and second images and the patient-specific brain atlas images. The additional image may be selected from gradient echo (GRE), fast spin echo (FSE), magnetic resonance angiography (MRA), diffusion weighted imaging (DWI), perfusion weighted imaging (PWI), and fluid-attenuated inversion-recovery (FLAIR) images.

Each one of the images may be two-dimensional (2D) or three-dimensional (3D). At least one of the first and second images may be a computerized tomography (CT) image.

In another aspect, a computer readable medium may be provided, which stores computer executable instructions. The computer executable instructions, when executed by a computer, adopt the computer to perform the above method.

In a further aspect, a computer may be provided, which comprises a processor and a computer readable medium. The computer readable medium stores computer executable instructions which, when executed by the processor, adopt the computer to perform the above method. The computer may comprise a display for displaying images.

Other aspects and features of the present invention will become apparent to those of ordinary skill in the art upon review of the following description of specific embodiments of the invention in conjunction with the accompanying figures.

BRIEF DESCRIPTION OF THE DRAWINGS

In the figures, which illustrate, by way of example only, embodiments of the present invention.

DETAILED DESCRIPTION

Figure 1:
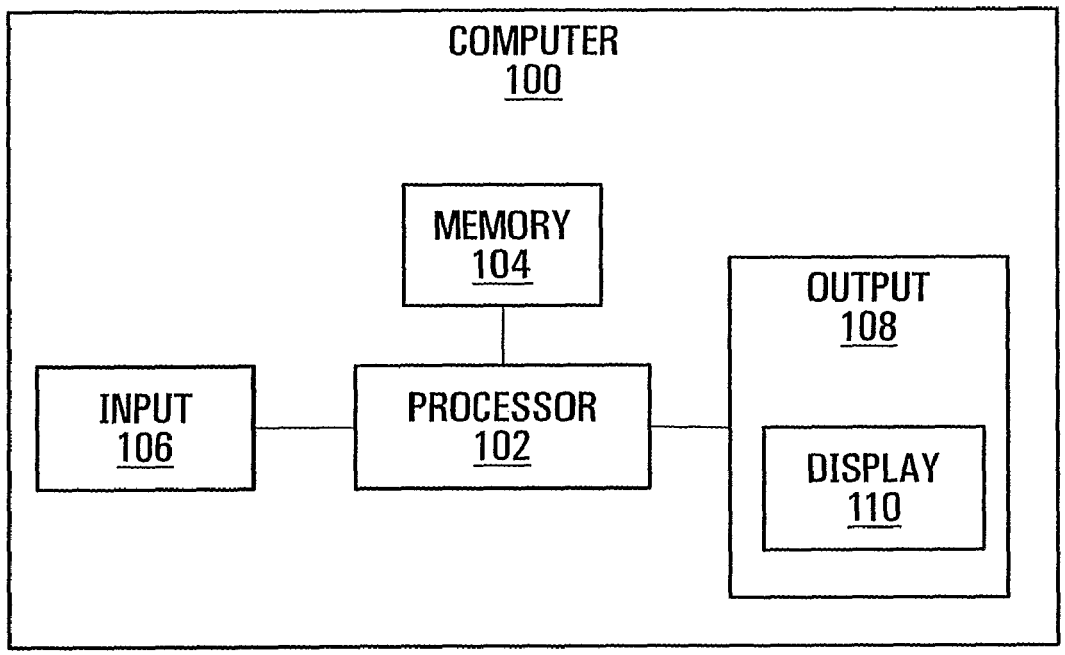
FIG. 1 is a schematic diagram of a computer, exemplary of an embodiment of the present invention.

As used herein, an "image" may include a brain image, a map image, an atlas image, or a superposition of these images. The term "image" may refer to a displayed image or stored image data for displaying the image. The image data may be stored in digital form on a computer readable medium, such as in an electronic image file. An image may be two-dimensional (2D) or three-dimensional (3D). In some applications, 3D images may provide better views and additional information may be obtained from 3D images. In some applications, 2D images may be easier to process and display, and thus can be processed quicker with less consumption of computing power.

A "brain image" refers to an image of a brain that is captured using an imaging device. A brain image may be a CT image, an MR image or another scanned image, or the like.

Each of the terms "map" and "atlas" is used herein in a broad sense, but generally refers to a map image or an atlas image, respectively. A brain map may refer to an image that is generated from a brain image. A map image may be used to determine infarct or penumbra regions. In such a case, the infarct and penumbra regions are still considered to be determined from the original brain images, although indirectly. A map may be a perfusion map. A region may be a 2D or 3D region depending on the context.

A brain atlas image, or brain atlas, refers to an image or collection of images for depicting one or more brain structures. A pre-existing brain atlas refers to a stored brain atlas. A pre-existing brain atlas is typically generic to different patients and may be used to form patient-specific brain atlas images based on brain images of individual patients. A pre-existing brain atlas may be any suitable known brain atlas that can assist stroke analysis. A patient-specific brain atlas image may be formed from a pre-existing brain atlas based on the brain images of the specific patient so that it is suitable for superimposing with the brain images of the specific patient to delineate the corresponding brain structures in the brain images. A brain structure may be any identifiable structural component of a normal brain, such as any anatomical structure or blood supply territories that may be affected by a stroke.

A map or atlas may have different representations. For example, a map or atlas may have a contour representation (e.g. a sequence of points or a bitmap) or an image representation. In a contour representation, the regions or structures in a map or atlas are delineated or depicted with contour lines or surfaces. In an image representation, the regions or structures in the map or atlas may be represented by photo-like image pixels or voxels. In a map or atlas, a region or structure may be delineated or depicted using any suitable marking schemes, such as by lines, colors, shades, and the like.

In an exemplary embodiment of the present invention, a number of images related to the brain of a patient are superimposed. The superimposed image may include diffusion and perfusion images of the brain, and patient-specific anatomy and vascular atlases. The brain images are co-registered to a co-ordinate system. The patient-specific brain atlases are formed by mapping pre-existing brain anatomy atlases and blood supply territories atlases to the same co-ordinate system. The mapping of the brain atlases may include landmark selection, resizing, scaling, warping, and the like. A patient-specific brain atlas image may be formed by modifying a stored brain atlas template so that it can be properly superimposed with the selected brain images and any other map or atlas. The superimposed image may also include contours for delineating the infract and penumbra regions in the superimposed image. The superimposed image may also include one or more brain maps, which are co-registered to the same co-ordinate system. The brain maps may include one or more of diffusion maps and perfusion maps. A diffusion map may be generated from a diffusion image of the brain. For instance, an apparent diffusion coefficient (ADC) map may be generated from two diffusion images. Contours for delineating infarct regions may be determined and generated from the diffusion image, or optionally from a diffusion map such as the ADC map. A perfusion map may be generated from a perfusion image of the brain. Exemplary perfusion maps include mean transit time (MTT), cerebral blood flow (CBF), cerebral blood volume (CBV), time to peak (TTP), and peak height (PKHT) maps. Contours for delineating the penumbra regions may be determined and generated from a perfusion map.

In contrast to conventional techniques of stroke diagnosis where multiple images are individually and separately inspected and analyzed, in this embodiment of the present invention, multiple brain and atlas images are superimposed to quickly identify and quantify the diffusion-perfusion mismatch, the infarct regions, and the underlying anatomy and blood supply territories. As can be understood, from the superimposed images and the quantities calculated as a result of the superposition, a user such as a medical doctor may be able to make an accurate diagnosis and form a suitable treatment plan, more quickly than doing so by merely visually inspecting separate brain images and brain atlases.

The superimposed image may be displayed, such as on a computer screen or the like. The displayed image shows the brain of the patient and infarct and penumbra regions in the brain. The image may be a superposition of two or more captured brain images and images generated from the captured images. For example, the captured brain images may include two or more of gradient echo (GRE), fast spin echo (FSE), magnetic resonance angiography (MRA), diffusion weighted imaging (DWI), perfusion weighted imaging (PWI), fluid-attenuated inversion-recovery (FLAIR), T1-weighted (T1W), T2-weighted (T2W) images, and the like. Images generated from the captured images may include one or more of the derived ADC, CBF, CBV, MTT, TTP, and PKHT maps. In a particular embodiment, the superposition may include a DWI image and a PWI image. The superposition may also include an angiography image such as an MRA image. As can be understood, a DWI image or an ADC MAP may show infarct regions in the brain, a PWI image or maps derived from the PWI image may show penumbra regions in the brain, and an MRA image may show the arteries of the brain, including narrowing or occlusion of the arteries.

The superimposed image may include one or more contours generated based on the brain image(s) for delineating the infarct and penumbra regions. For example, an infarct contour generated based on the diffusion image and a penumbra contour generated based on the perfusion image may be included. In one embodiment, these contours may delineate a region of a present infarct and a region of a prior infarct in the brain image, and a region of an apparent penumbra in the brain image. In a different embodiment, the contours may delineate a region of a present infarct and a region of a prior infarct in the brain image. In a further embodiment, the contours may delineate a region of an apparent penumbra in the brain image.

In different embodiments, the patient-specific brain atlas images include one or more atlases for depicting one or more brain structures. For instance, the brain atlas images may include a BST atlas image to show blood supply territories in the brain image, and an anatomy atlas image to show anatomical structures in the brain image.

As the brain images and atlas images are co-registered and superimposed, any and all overlap between the infarct/penumbra regions and the brain structures depicted by the brain atlas images may be visible and identifiable. Mismatch may be quickly identified. For example, incorrect or inaccurate segmentation or delineation may be quickly identified and corrected interactively. As a result, a stroke diagnosis may be quickly made by a medical professional.

Exemplary embodiments of the present invention include methods or processes as described above. These methods can be performed, at least in part, by a computing device such as a computer 100 for image processing shown in FIG. 1, exemplary of an embodiment of the present invention.

Computer 100 has a processor 102, which communicates with primary memory 104, input 106 and output 108. Computer 100 may optionally communicate with a network (not shown) or another device (not shown).

Processor 102 can be any suitable processor including microprocessors, as can be understood by persons skilled in the art. Processor 102 may include one or more processors for processing data and computer executable codes or instructions.

Memory 104 may include a primary memory readily accessible by processor 102 at runtime. The primary memory may typically include a random access memory (RAM) and may only need to store data at runtime. Memory 104 may also include a secondary memory, which may be a persistent storage memory for storing data permanently, typically in the form of electronic files. The secondary memory may also be used for other purposes known to persons skilled in the art. Memory 104 can include one or more computer readable media. For example, memory 104 may be an electronic storage comprising a computer readable medium for storing electronic data including computer executable codes. The computer readable medium can be any suitable medium accessible by a computer, as can be understood by a person skilled in the art. A computer readable medium may be either removable or non-removable, either volatile or non-volatile, including any magnetic storage, optical storage, or solid state storage devices, or any other medium which can embody the desired data including computer executable instructions and can be accessed, either locally or remotely, by a computer or computing device. Any combination of the above is also included in the scope of computer readable medium. Memory 104 may store computer executable instructions for operating computer 100 in the form of program code, as will be further described below. Memory 104 may also store data such as operational data, image data, input data, and output data.

Input 106 is to be broadly interpreted and may include user input devices for receiving user input such as image data and operation commands. Example user input devices may include a keyboard, a mouse, a disk drive/disk, a network communication device, a microphone, a scanner, a camera, and the like. Input 106 may also include sensors, detectors, or imaging devices for capturing, for example, an image. Input 106 may also include a communication device for communicating with a separate imaging device and receiving image data from the imaging device. Input 106 may communicate with another computer or device through wired or wireless communication, as can be understood by persons skilled in the art. An input device can be locally or remotely connected to processor 102, either physically or in terms of communication connection.

Similarly, output 108 is also to be broadly interpreted. Output 108 may include a display device 110 such as a monitor for displaying output data, a printer for printing output data, a communication device for communicating output data to another computer or device, and the like, as can be understood by persons skilled in the art. Output 110 may also include other devices such as a computer writable medium and the device for writing to the medium. Like input devices, an output device can be local or remote.

It will be understood by those of ordinary skill in the art that computer 100 may also include other, either necessary or optional, components not shown in the FIG. 1.

The hardware in computer 100 may be manufactured and configured in any suitable manner, including that for a conventional computer with the exception that images are processed differently in computer 100 as will be described below. As can be understood, the imaging processing methods and algorithms may be implemented with either hardware, or a combination of hardware and software.

Memory 104 may store thereon computer executable code or instructions, which when executed by processor 102 can adopt computer 100 to carry out or perform any of the methods described herein or one or more steps of these methods. The software for use in computer 100 may be readily developed and implemented by persons skilled in the art after reading this paper. As can be appreciated, methods described herein can also be carried out using a hardware device having circuits for performing one or more of the described calculations or functions.

Figure 2:
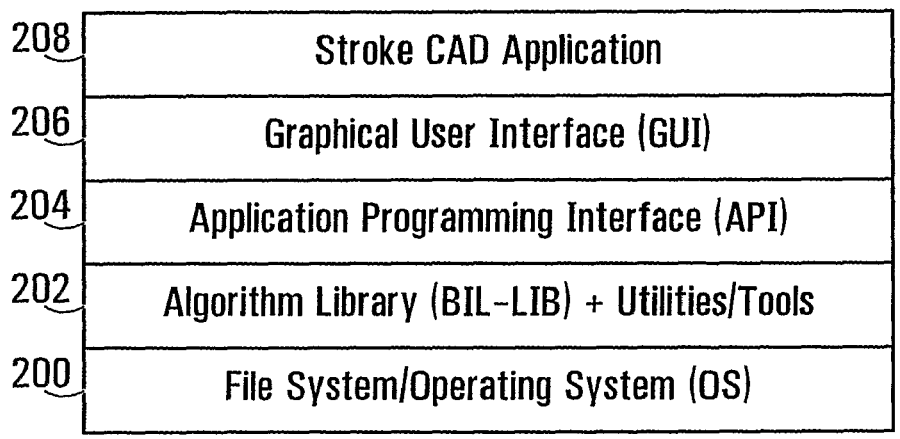
FIG. 2 is a block diagram illustrating a software architecture for software stored on the computer in FIG. 1.

For example, memory 104 may store computer software that has an architecture illustrated in FIG. 2. As shown, the software may include a file system and an operating system (OS) 200. Exemplary operating systems include Microsoft Windows™, Microsoft Vista™, Apple Mac™ OS, Unix, Linux, and the like. The next layer may include runtime libraries, utilities and tools. The runtime library may include an Algorithm Library 202 such as the Biomedical Imaging Lab Library (BIL-LIB) and other software utilities and tools. As is typical, the software may also include application programming Interfaces (API) applications 204 and graphical user interface applications 206. The top level is a Stroke Computer-aided diagnosis (CAD) application 208, which will be further described below. Any of these applications may be coded in any suitable computer language and using any suitable programming technique. For example, the BIL-LIB library is written in C++ using the object-oriented programming technique.

In some cases, a computer-aided diagnosis application may support the following workflow, which will not be fully described in detail herein:

Load case (multiple studies)
View individual studies (to exclude hemorrhage and/or identify any previous infarct)
Process diffusion (to segment and quantify the infarct)
Process perfusion (to segment and quantify the penumbra)
Process 3D angiographic image (to identify/exclude vessel occlusion)
Quantify the diffusion-perfusion mismatch
Perform atlas-assisted analysis (including the infarct-MCA ratio calculation).

Figure 3:
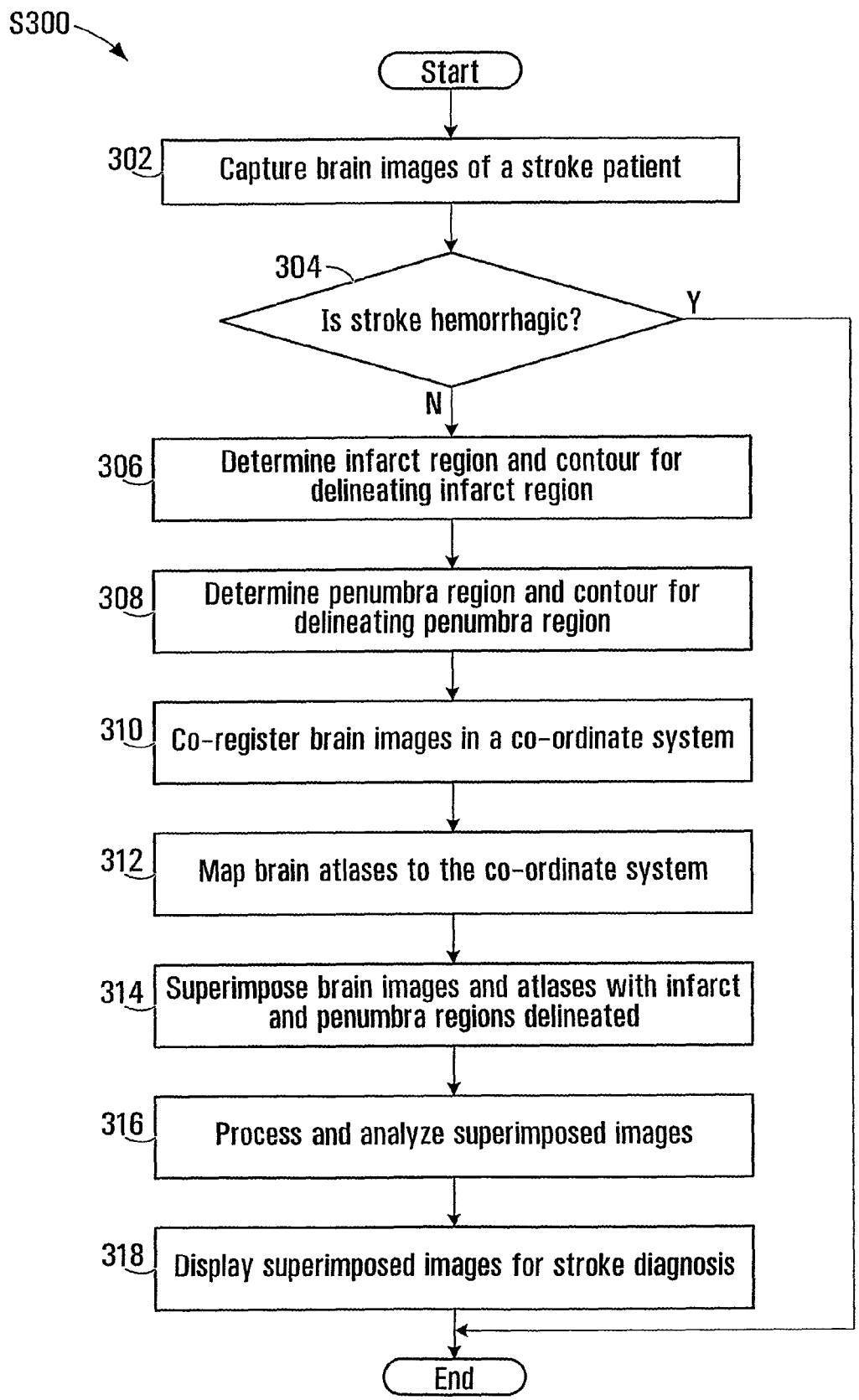
FIG. 3 is a flowchart for a process performed by the computer of FIG. 1, exemplary of an embodiment of the present invention.

FIG. 3 is a flowchart illustrating a process S300 performed by CAD application 208.

At S302, multiple brain images of a patient may be obtained. The images of the patient's brain may be captured by scanning or another suitable imaging technique. A captured brain image may be subject to post-capture processing or alteration, such as removal of noise or background, intensity correction including field inhomogeneity correction, and the like. The post-capture processing or alteration may be performed automatically by a computer or interactively with input from a user. Some of the captured brain images, either unaltered or altered, may be displayed, such as on display 110 of computer 100. The user may select the brain images to be displayed at any given time.

The brain images may include scanned images selected from GRE, FSE, MRA, DWI, PWI, T1W, T2W and FLAIR images. Different types of brain images may be obtained for different purposes and not all of them need to be later superimposed with the atlas images. For example, a GRE image may be used to exclude hemorrhagic stroke. A DWI image may be used to determine infarcts. A FLAIR or T2W image or a ADC map may be used for staging. A PWI and maps derived from it may be used to determine penumbra. An MRA image may be used to determine occlusion. In one embodiment, a diffusion image and a perfusion image are captured. As can be appreciated, the diffusion image may include a DWI image. The perfusion image may include a PWI image. Other suitable images, such as an MRA image, may also be captured. The captured images may be stored, such as on memory 104, for later processing.

At S304, the brain images are analyzed to determine if the stroke is hemorrhagic. In one embodiment, this determination may be made based on analysis of a GRE image and a FSE image. CAD application 208 may provide a routine for automatically segmenting a region from the GRE image, such as based on an intensity threshold. CAD application 208 may also provide a routine for automatically segmenting a region from the FSE image, such as based on an intensity threshold. The segmented GRE and FSE regions are analyzed to determine if the former is larger than the latter. The segmented regions may be superimposed for such determination. For example, the images points such as pixels and voxels of the images may be co-registered to a same co-ordinate system.

As can be understood by persons of skill in the art, image segmentation is a common technique used for tissue classification or identification in brain image analysis. The classification or segmentation of a particular tissue is typically based on a property of the tissue in the image and may be performed in various suitable manners depending on the tissue and its properties. One of the common techniques is the intensity thresholding technique. For example, the intensities of the image points, either pixels or voxels, may be used to segment the image by excluding image points that have intensities less than (or higher than) an appropriate threshold intensity.

The segmentation process may be performed automatically using a computer such as computer 100. The computer algorithms for segmentation may include functions for automatic threshold selection and adjustment to improve processing speed and accuracy.

If the segmented GRE region is larger than the segmented FSE region, then the stroke is determined to be hemorrhagic, in which case, process S300 may terminate. Otherwise, the stroke is determined to be ischemic and process S300 may continue to S306.

In different embodiments, the brain images may be, at least in part, visually inspected and manually processed to determine if the stroke is hemorrhagic or ischemic.

At S306, the infarct regions are determined and infarct contours may be generated. For example, one or more diffusion images, such as a DWI image, may be used for this purpose.

Before the DWI image is processed to determine the infarct regions, certain artifacts, such as susceptibility artifacts, on the image may be identified and then corrected, reduced or removed.

CAD application 208 may have a routine for automatically segmenting an infracted region from the DWI image, such as by using an adaptive intensity threshold.

The segmentation of the DWI image may be performed in several steps. For example, a DWI image may be initially automatically segmented as a whole (global segmentation), such as using a supervised range-constrained thresholding technique as described in Q. Hu et al., "Supervised range-constrained thresholding", *IEEE transactions on Image Processing,* 2006, vol. 15, pp. 228-240, the contents of which are incorporated herein by reference. The segmented regions may be further processed to remove isolated regions using a fast connected-component labeling technique as described in Q. Hu et al., "Fast connected-component labeling in three dimensional binary images based on iterative recursion", *Computer Vision and Image Understanding,* 2005, vol. 99, pp. 414-434, the contents of which are incorporated herein by reference. One or more infarct contours may be generated for delineating the segmented infarct regions.

Next, if the global segmentation is not sufficiently satisfactory, such as due to the selection of an inaccurate threshold or an inherent limitation of the thresholding technique, the segmentation may be improved through semi-automatic local thresholding. For instance, an region of interest may be selected, such as interactively, and the selected region, such as a local volume or a slice, may be segmented using thresholds determined either automatically or interactively for the region of interest. In one embodiment, the DWI image is delineated with the initial infarct contour. The delineated image may be displayed for visual inspection, as illustrated in FIG. 4.

Figure 4:
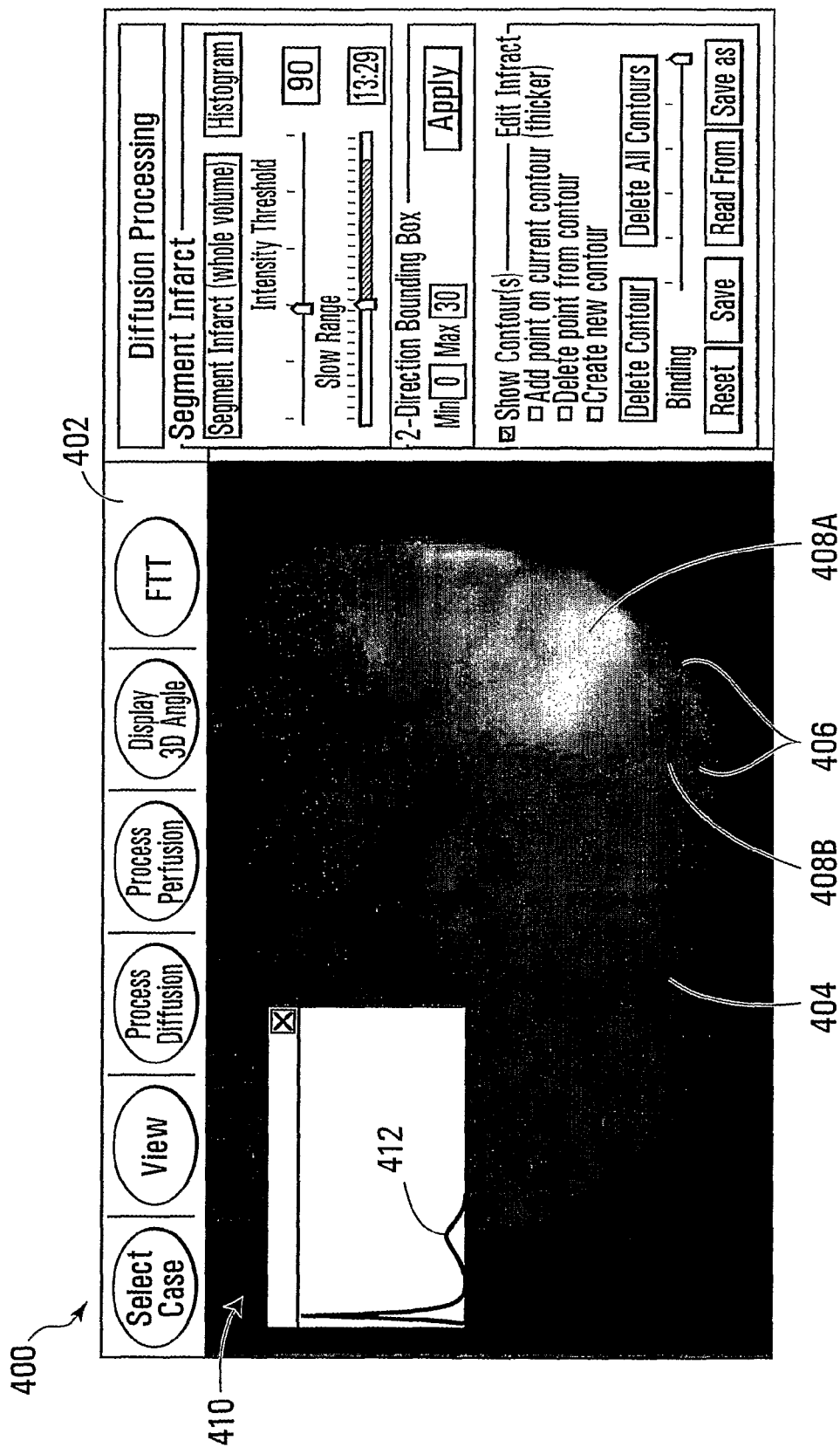
FIGS. 4 to 8 are screenshots of the computer display of FIG. 1, showing exemplary brain images and delineated infarct and penumbra regions.

FIG. 4 shows an exemplary screenshot 400 of a graphical user interface (GUI) 402 for CAD application 208, which is displayed on computer display 110 of computer 100. In GUI 402, a scanned DWI image 404 is shown, along with contour lines 406 delineating infarct regions 408A and 408B. Infarct regions are also individually or collectively referred to herein as infarct region(s) 408. For convenience of adjusting the threshold to improve segmentation, an intensity histogram 410 of the image points is also shown in GUI 402, where the horizontal axis is the intensity and the vertical axis is the number of image points. The lower peak 412 in histogram 410 corresponds to the infarct regions 408. As can be appreciated, an appropriate intensity threshold for segmenting the infarct regions 408 may be selected from the valley region between the two peaks in histogram 410. A user may dynamically adjust the value of the threshold to adjust the contours of the infarct regions and inspect the modified view to see if any improvement has been made to the segmented image.

Figure 5:
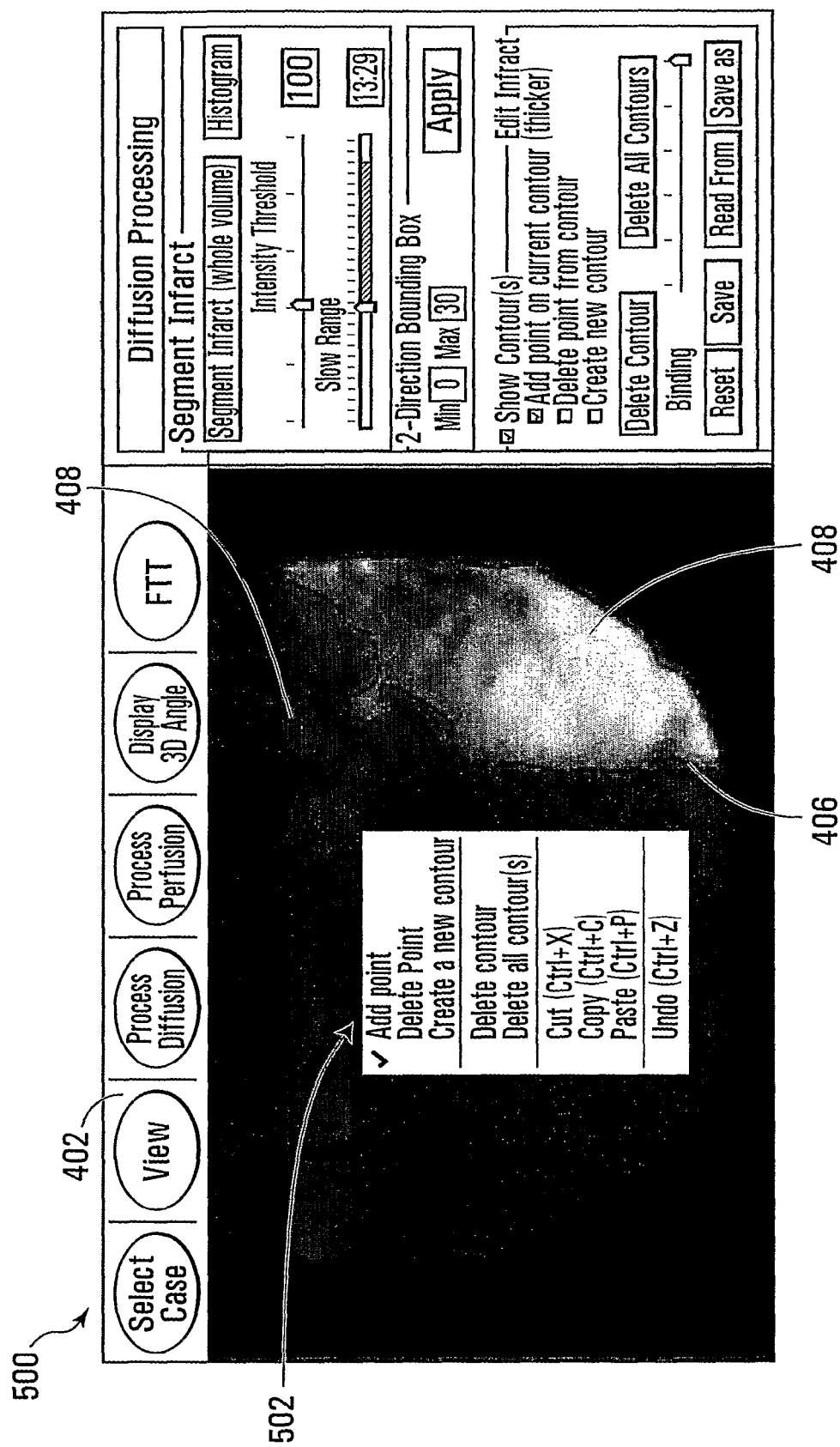

In addition, or alternatively, the user may interactively move, add, or delete contour points or entire contour lines directly from the displayed image. The displayed image may be enlarged, or zoomed, and panned to allow more precise adjustment of the contours. For instance, FIG. 5 shows another screenshot 500 of GUI 402, where a pull-down menu window 502 is shown. As can be seen, the menu provides menu items for modifying the contour lines 406 that enclose the infarct regions 408. As can be seen, the menu options include add point, delete point, create a new contour, or delete contour(s).

As can be understood, segmentation of a 3D image may be carried out by segmenting and adjusting infarct regions in all 2D slices of the 3D image, on a slice-by-slice basis. Alternatively, one or more representative 2D slices may be selected and segmented. The segmented 2D slices may be combined or otherwise used to construct a 3D segmented image. For instance, a segmented 3D image may be constructed by generating a binary volume from the image points within the contours of the determined infarct regions and applying a Marching Cubes algorithm to the binary volume, according to the method described in W. E. Lorensen et al., "Marching Cubes: A high resolution 3D surface construction algorithm," *Computer Graphics,* 1987, vol. 21, pp. 163-169, the contents of which are incorporated herein by reference.

If necessary, the initial contours for a 3D image may be further revised or corrected, either automatically or interactively. For instance, the 3D brain image and contours may be sliced along any axis. The contours may also be corrected in 3D directly. The contours can also be interpolated.

The segmented 3D image may be displayed and manipulated, such as rotated, zoomed or panned, in three dimensions. An exemplary segmented 3D image is shown in the screenshot 600 of FIG. 6. On the right-hand side of FIG. 6, a 2D image 602 is shown, which is a superposition of a 2D brain image and 2D infarct contours that delineate infarct regions 604 with contour lines 606. On the left-hand side, a 3D surface 608 is shown, which represents a 3D infarct volume constructed based on the 2D contour on the right. The plane 610 beside 3D surface 608 represents the midsagittal plane of the brain, which is useful for referencing. The partially shown box 612 outlined by the lines 614 is a brain bounding box (BBB). The BBB is a box that encloses the largest connected component in a brain image. This component is considered as the brain and thus the BBB is expected to enclose the brain. The BBB along with the directions marked can thus be used as a reference frame for orienting and positioning different brain images and patient-specific brain atlas images for the same brain in space so that they are properly superimposed.

A 3D image of the infarct volume, such as 3D surface 608, may be useful to show the spatial relationship among the infarct regions or infarct contours in adjacent and consecutive 2D image slices, and may be useful for making further adjustments of the 2D contours. The volume of the 3D infarct region may be calculated and displayed, such as illustrated at the bottom right corner of FIG. 6, the use of which will be discussed below. The volume value may be updated continuously such as recalculated after the infarct region contours have bee adjusted.

Figure 6:
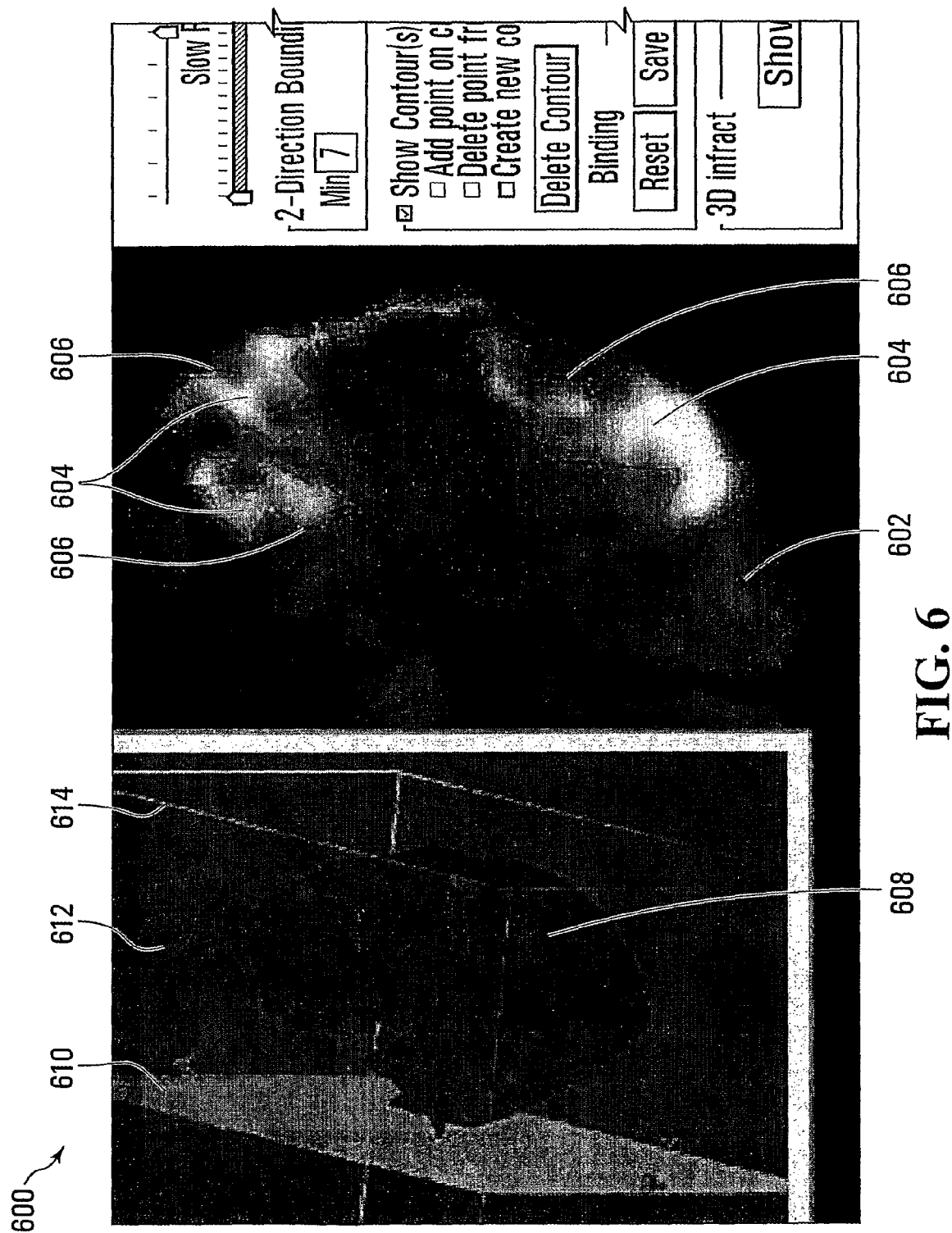

In FIGS. 4 to 6, the 2D infarct contours that contain contour lines 406 or 606 are superimposed with the brain images for delineating the infarct regions 408 or 604. 3D surface 608 may also be superimposed with a corresponding 3D brain image to delineate the 3D infarct volume therein.

In some embodiments, a suitable conventional technique for identifying and segmenting the infarct regions may be used, and the infarct contours may be constructed or generated accordingly. In other embodiments, dedicated or specifically developed techniques may be used for segmenting the infarct regions.

As can be appreciated, for proper stroke diagnosis it may be useful to determine both present infarct and prior infarcts, so that all the actual infarct may be determined. To do so, an apparent diffusion coefficient (ADC) map may be generated from a DWI image, and the ADC map and the DWI image may be compared to determine any prior infarct regions, as can be readily understood by persons skilled in the art. Actual infarct regions may be determined by superimposing the ADC map with the DWI image or the infarct contours, or otherwise combining the present and prior infarct regions identified from the DWI image and the ADC map. In one embodiment, a present infarct region may be determined from the DWI image. A present-infarct contour may be generated for delineating the present infarct region. The DWI image and the ADC map may be superimposed to determine the prior infarct region. A prior-infarct contour may be generated for delineating the prior infarct region. The actual infarct region may be determined or formed by combining the prior infarct region and the present infarct region, such as by adding these regions, or combining or superimposing the two contours. In one embodiment, the final superimposed image may include an infarct contour for delineating the actual infarct region. In another embodiment, the final superimposed image may include multiple infarct contours that delineate the present and prior infarct regions respectively.

At S308 of FIG. 3, penumbra regions of the brain are determined from a suitable brain image. Penumbra contours for delineating the penumbra regions may be generated from the brain image. For example, one or more perfusion maps may be used for determining the penumbra regions and generating the penumbra contours. In one embodiment, the perfusion image may include a PWI image. In some applications, it may be necessary or desirable to remove any artifacts and/or geometric distortions from the brain images before segmentation. The penumbra regions may be segmented either automatically or interactively, or both. For instance, the PWI image may be automatically and globally segmented using a suitable thresholding technique. In one embodiment, a mean transit time (MTT) map is generated based on the PWI image. The penumbra regions may be segmented by segmenting the MTT map using a given time as the threshold. The time threshold may be selected interactively. A suitable conventional technique for identifying and segmenting penumbra regions may be used.

Other perfusion maps may also be generated from the perfusion image for segmenting and delineating the penumbra regions. Useful perfusion maps may include MTT, CBF, CBV), TTP, and PKHT maps.

In some embodiments, segmentation of the penumbra regions may be facilitated by delineating the infarct regions on the perfusion maps, as will be further discussed below.

Figure 7:
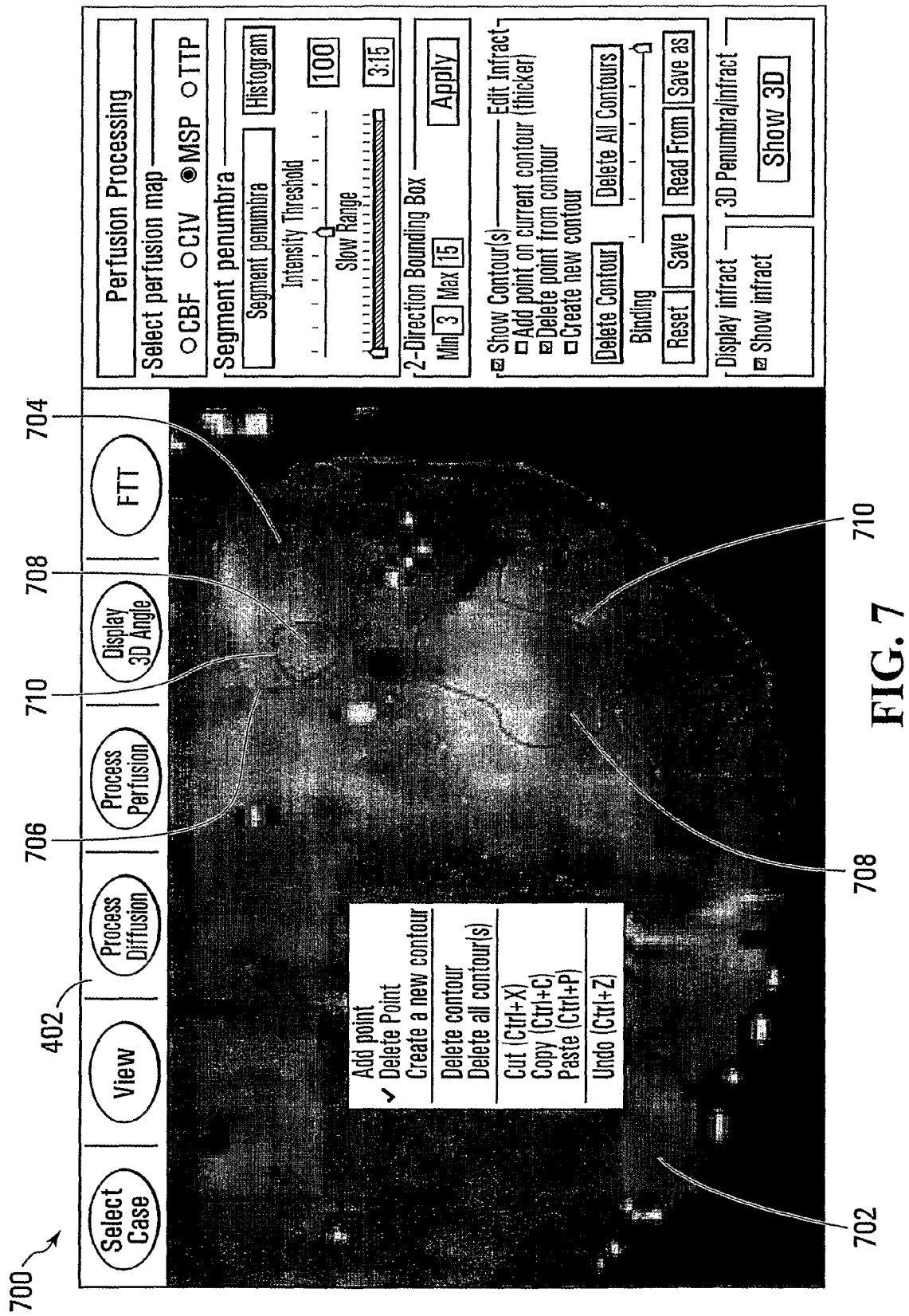

FIG. 7 shows an exemplary screenshot 700 that has a superimposed image 702 which includes a MTT map along with the infarct and penumbra contours. A penumbra region 704 is delineated by contour line 706. Superimposed image 702 also includes an infarct contour which delineates the infarct regions 708 with contour lines 710. The contour line 706 may be interactively modified, similar to the case of the infarct contours discussed above.

Like segmentation of the infarct regions, the penumbra regions may be segmented from the brain image in 2D or 3D. When initially segmented in 2D, the 2D contours may be used to construct 3D contours. Alternatively, multiple 2D contours may be displayed in corresponding spatial relationship to show a 3D penumbra volume.

Figure 8:
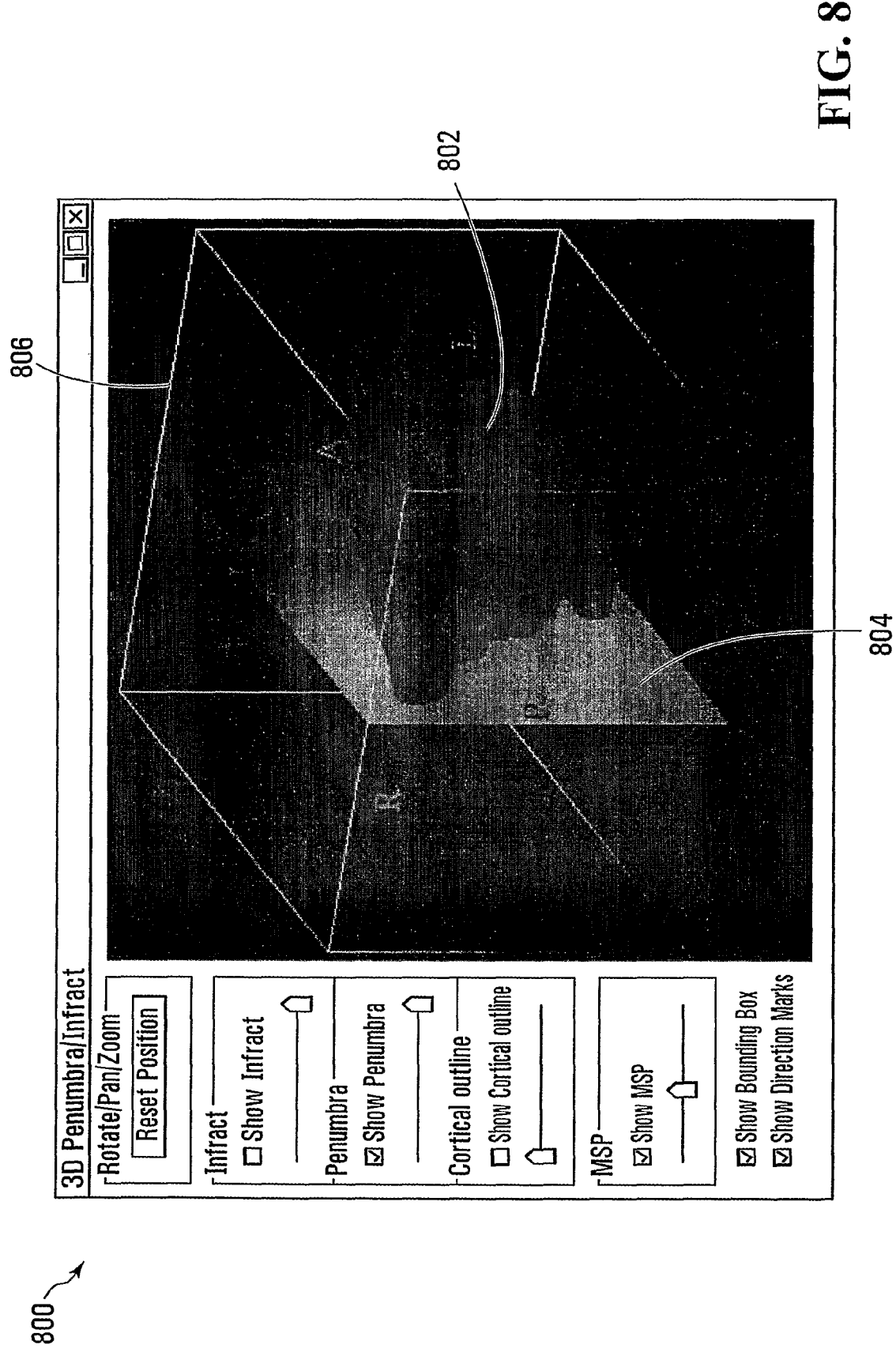

FIG. 8 is a screenshot 800 that shows an exemplary 3D image 802 of a segmented penumbra region. A midsagittal plane 804 and a brain bounding box 806 are also shown, similar to those shown in FIG. 6.

The volume of any 3D penumbra region may be calculated and displayed, the use of which will be apparent to persons skilled in the art. As can be understood, the actual penumbra region may be formed by first determining the overlaps between the actual infarct regions and apparent penumbra regions, and then excluding the overlapped regions from the apparent penumbra regions. Consequently, the volume of the actual penumbra may be calculated by subtracting the volume of any overlap between the actual infarct and the apparent penumbra from the volume of the apparent penumbra.

At S310 of FIG. 3, the brain images, with the contours for delineating the actual infarct and penumbra regions, are co-registered to a co-ordinate system. Any suitable co-ordinate system may be used. For example, a 2D or 3D Cartesian or Talairach co-ordinate system may be used. Such co-registration may be readily performed by one skilled in the art, such as according to a suitable conventional technique for co-registering images to a same co-ordinate system.

At S312 of FIG. 3, pre-existing brain atlases for depicting brain structures are obtained and mapped to the co-ordinate system to form the patient-specific brain atlas images. The pre-existing brain atlases may include a BST atlas for delineating or depicting the BST on a brain image, and an anatomy atlas for delineating or depicting the anatomical structures such as bones in a brain image. The anatomy atlas may depict subcortical structures and cortical areas, such as gyri and Brodmann's areas. These pre-existing atlases may be deterministic where the borders between different structures are definite, or probabilistic where the borders are fuzzy. The pre-existing brain atlases may be obtained, such as retrieved from an electronic storage, e.g. memory 104 or a remote storage.

The pre-existing atlases are electronically generated, and adjusted or modified to form the patient-specific brain atlas images, at least in part, based on the corresponding brain images and the co-ordinate system in which the brain images are co-registered. A pre-existing brain atlas may be a brain atlas template or a standard brain atlas. The patient-specific brain atlas image is formed by transforming an atlas image of the pre-existing brain atlas so that it can be properly superimposed with the corresponding brain images and any other corresponding map and atlas images. To properly superimpose the patient-specific brain atlas images with the captured brain images, the pre-existing brain atlases may need to be transformed or otherwise modified to match the co-registered brain images, such as in location, size, orientation, shape and the like. Two exemplary techniques may be used for mapping the pre-existing brain atlases to the co-ordinate system.

In one embodiment, the pre-existing brain atlases are transformed using the Fast Talairach Transformation (FTT) technique. In another embodiment, the pre-existing brain atlases are modified by using the midsagittal plane (MSP) and matching them to the brain's bounding box (BBB). These techniques have been described in detail in W. L. Nowinski et al., "Rapid and automatic calculation of the midsagittal plane in magnetic resonance diffusion and perfusion images," *Academic Radiology*, 2006, vol. 3, pp. 652-663, the contents of which and the references cited therein are incorporated herein by reference.

Figure 9:
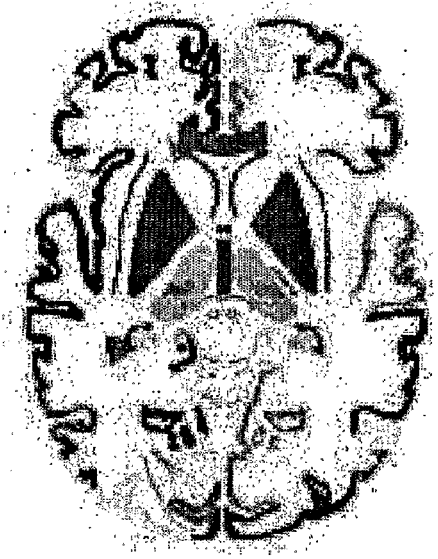
FIGS. 9 to 11 are images of exemplary brain atlases.
Figure 10:
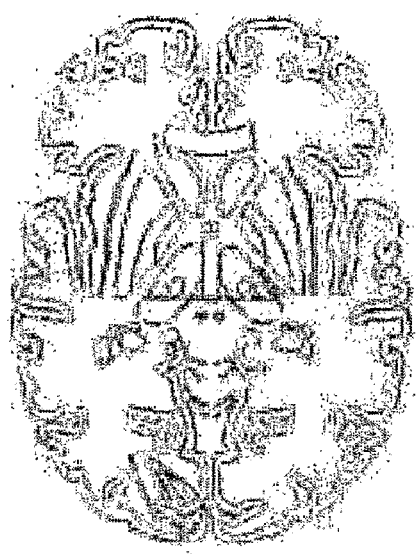

An exemplary patient-specific anatomy atlas is shown in FIGS. 9 and 10. The anatomy atlas is shown in image representation in FIG. 9 and in contour representation in FIG. 10. The anatomy atlas is formed from a Cerefy brain atlas according to the technique described in W. L. Nowinski et al., *The Cerefy Clinical Brain Atlas on CD-ROM*. Thieme, New York, 2004, the contents of which are incorporated herein by reference. The Cerefy atlas is derived from the Talairach-Tournoux (TT) brain atlas of gross anatomy described in Talairach et al., *Coplanar Stereotactic Atlas of the Human Brain*, Thieme, Stuttgart-New York, 1988, the contents of which are incorporated herein by reference. The patient-specific anatomy atlas image may also be modified, enhanced, or improved according to the techniques described in W. L. Nowinski et al., "Multiple brain atlas database and atlas-based neuroimaging system," *Computer Aided Surgery*, 1997, vol. 2, pp. 42-66; W. L. Nowinski, "Electronic brain atlases: features and applications," in 3*D Image Processing: Techniques and Clinical Applications*, Medical Radiology series, eds. D. Caramella and C. Bartolozzi, Springer-Verlag, 2002, pp. 79-93; W. L. Nowinski, "The Cerefy brain atlases: continuous enhancement of the electronic Talairach-Tournoux brain atlas," *Neuroinformatics*, 2005, vol. 3, pp. 293-300; and W. L. Nowinski, "Modified Talairach landmarks," *Acta Neurochir*, 2001, vol. 143, pp. 1045-1057, the contents of each of which are incorporated herein by reference.

The Cerefy atlas may be labeled or annotated. In one embodiment, the Cerefy atlas may be labeled with all 138 white and gray matter structures. Such a pre-existing atlas is available in both image and contour representations. The contour representations may be advantageous in some applications as they facilitate visual viewing of superimposed images.

The Cerefy atlas may be further modified based on a captured brain image to form the patient-specific brain atlas image suitable for superimposing with the captured image to depict or delineate the anatomy structures.

The pre-existing BST atlas may depict the following seven BST:

penetrating branches of anterior cerebral artery (ACA)
terminal branches of ACA
penetrating branches of MCA
terminal branches of MCA
penetrating branches of posterior cerebral artery (PCA) and posterior communicating artery
terminal branches of PCA
anterior choroidal artery.

In one embodiment, the pre-existing BST atlas may be derived partly from a BST template described in H. J. Kretschmann et al., *Cranial Neuroimaging and Clinical Neuroanatomy*, 3rd ed. Thieme, Stuttgart, 2004, the contents of which are incorporated herein by reference. Briefly, the patient-specific BST atlas image may be constructed as follows. The axial BST templates are digitized. Brain regions are extracted from the digitized templates. The digitized templates are registered nonlinearly with the axial images of the patient-specific anatomy atlas image. The fit between the templates and the patient-specific anatomy atlas may be further enhanced automatically as described in the above cited references. The formed patient-specific BST atlas image may be edited interactively by a user.

Figure 11:
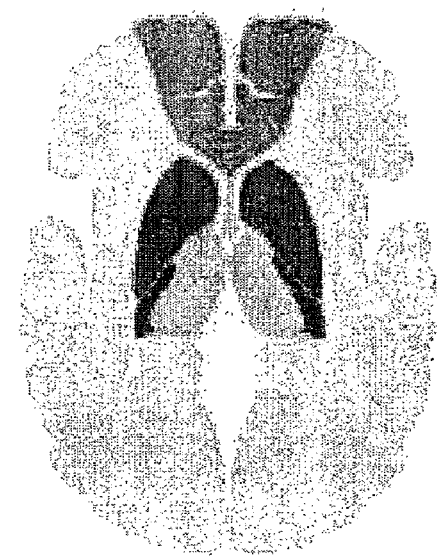

Similarly to the pre-existing anatomy atlas, the pre-existing BST atlas may be in either image or contour representations. Accordingly, the patient-specific anatomy atlas image or BST atlas image may also be in either image or contour representation. An exemplary patient specific BST atlas image in image representation is shown in FIG. 11.

The patient-specific BST atlas may be constructed such that it is suitable for superimposing with the corresponding patient-specific anatomy atlas image and is of the same image format as the anatomy atlas image.

In some embodiments, two sets of images or atlas images may be considered to correspond to each other or suitable for superimposing with each other when they satisfy the following conditions:

1. Both sets of images have the same image size and resolution, and the same number of associated atlas images;
2. Both sets of atlas images have the same shape of the cortex and ventricular system; and
3. Both sets of atlas images are located in the same (e.g. Talairach) coordinate system.

Figure 12:
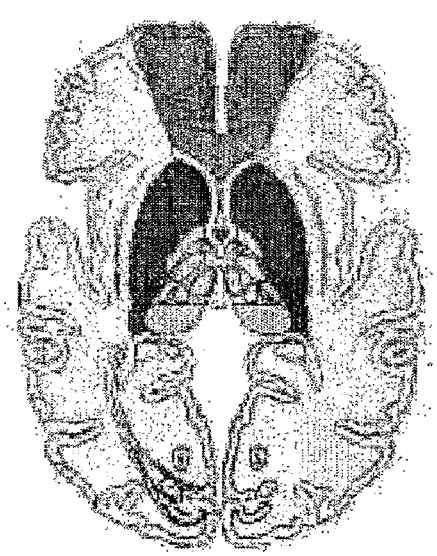
FIG. 12 is a superimposed image of the brain atlases in FIGS. 10 and 11.

A superposition of the anatomy atlas in FIG. 10 and the BST atlas in FIG. 11 is shown in FIG. 12.

As can be appreciated, to accurately match the captured brain images, the brain atlases may need to be modified such as resized or co-registered to correspond with the captured brain images. As discussed above, the FTT technique may be used to quickly and automatically map the pre-existing atlases to the captured brain images, or to the co-ordinate system in which the captured brain images are co-registered. It has been found that the FTT technique can automatically map a pre-existing anatomy atlas onto a T1-weighted image in about 5 seconds. The landmarks used in the FTT may be calculated automatically in three steps: (i) calculate the MSP, (ii) identify the anterior commissure (AC) and posterior commissure (PC) landmarks, and (iii) calculate the cortical landmarks. The steps (i), (ii) and (iii) may be respectively carried out according to the techniques described in Q. Hu et al., "A rapid algorithm for robust and automatic extraction of the midsagittal plane of the human cerebrum from neuroimages based on local symmetry and outlier removal," *Neuroimage*, 2003, vol. 20, pp. 2154-2166; B. P. K. N. et al., "Rapid and automatic localization of the anterior and posterior commissure point landmarks in MR volumetric neuroimages," *Acad Radiol*, 2006, vol. 13, pp. 36-54; Q. Hu et al. "Fast, accurate, and automatic extraction of the modified Talairach cortical landmarks from magnetic resonance images," *Magn Reson Med*, 2005, vol. 53, pp. 970-6; PCT patent application publication number WO 2005/096227 to K. N. et al., published Oct. 13, 2005; and PCT patent application publication number WO 2005/048844 to Nagaraja Rao et al., published Jun. 2, 2005, the contents of each of which are incorporated herein by reference.

After transformation as described above, the captured brain images may be reformatted along the AC-PC plane and the transformed atlases may be scaled piecewise linearly to form the patient-specific atlas image, which is then superimposed with the brain images.

Figure 13:
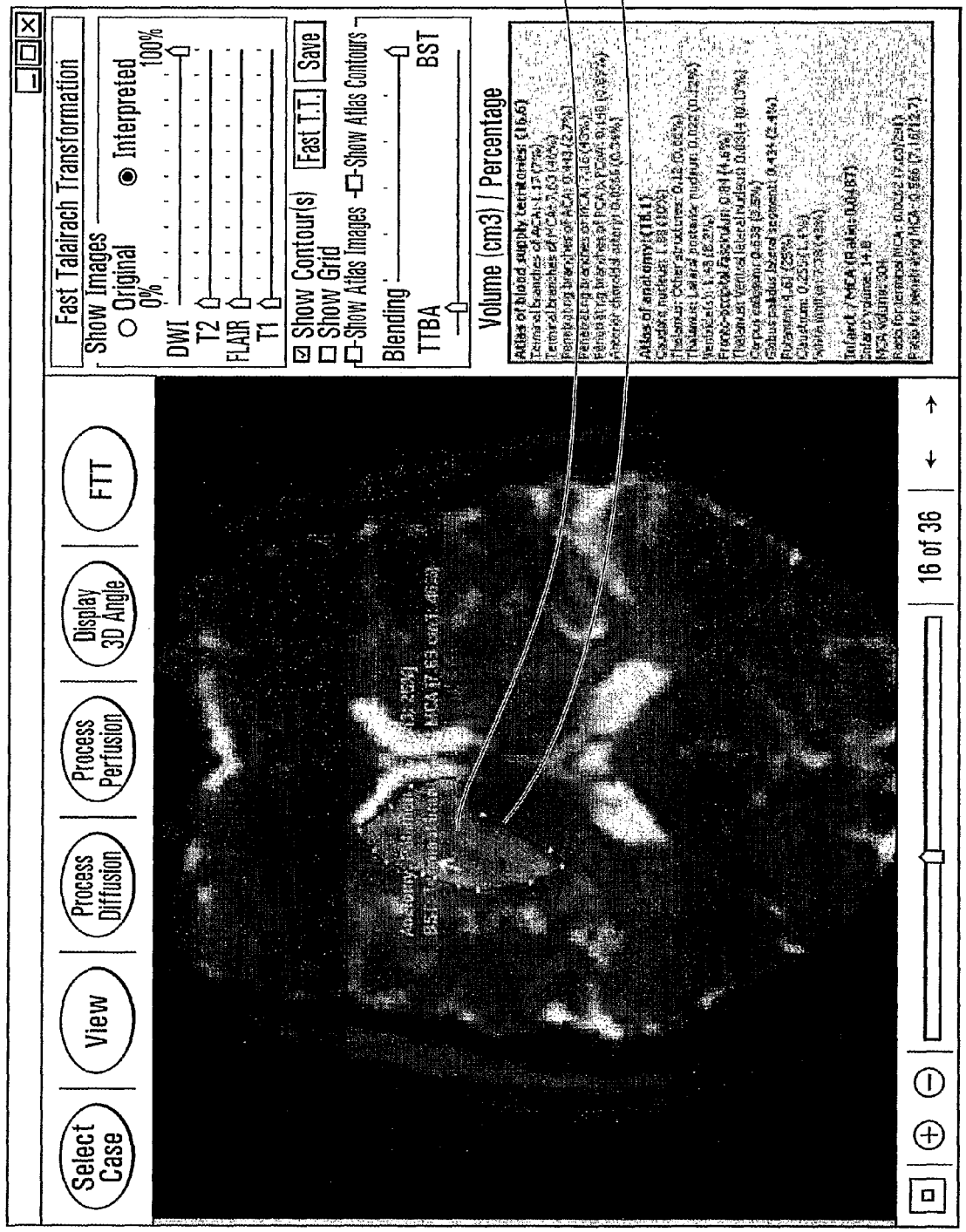
FIG. 13 is a screenshot showing an exemplary superimposed image of brain images and atlases with a contour delineating an infarct region, and quantification data calculated based on the superimposed image.

An exemplary superposition of brain images and atlas images, based on the FTT technique, is shown in the screenshot of FIG. 13. The brain images in the superposition include 2D DWI and T1-weighted images acquired along a same plane. The superposition also includes an infarct contour 1302 for delineating the infarct region 1304. The anatomy and BST labels shown are obtained from the corresponding patient-specific anatomy and BST atlas images (not shown, but see FIGS. 14 and 15), which, although not shown, are also co-registered with the DWI and T1-weighted images. As illustrated in FIG. 13, the names or other similar identification data of the anatomy and vascular structures that overlap with the infarct regions may be displayed, such as in the right-panel of the GUI.

Figure 14:
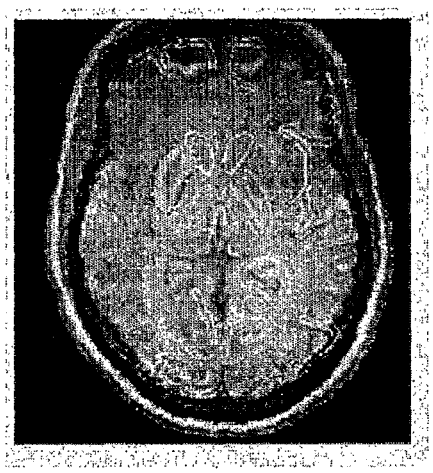
FIGS. 14 and 15 are respectively exemplary superimposed images of brain images, infarct contours and a brain atlas in contour representation.
Figure 15:
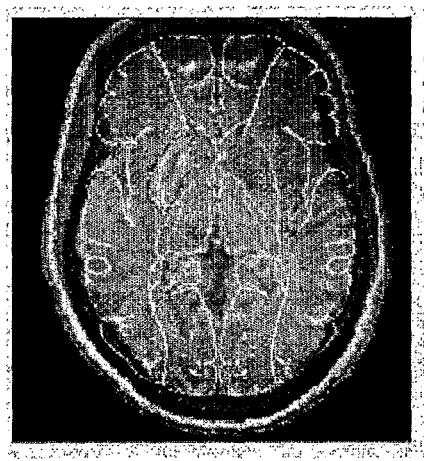

FIG. 14 shows a superposition where the patient-specific anatomy atlas image in the contour representation is superimposed with the brain images and the contour for delineating the infarct region, but the BST atlas is omitted. FIG. 15 is a similar superposition but the patient-specific BST atlas image is displayed instead of the anatomy atlas image. CAD application 208 may allow a user to select different blending ratios to vary the visibility of different atlas images.

In cases where a T1-weighted scanned image is not available or data reformatting is not desirable, the captured diffusion and perfusion images and the brain atlases may be matched, co-registered, or superimposed together by aligning their MSPs first and then scaling their BBBs so that the BBBs match each other in size. The MSPs of the brain images and atlas images may be aligned according to the technique described in W. L. Nowinski et al., "Atlas-assisted MR stroke image interpretation by using anatomical and blood supply territories atlases," *Program*, 91$^{st}$ Radiological Society of North America Scientific Assembly and Annual Meeting RSNA 2005, Chicago, Ill., USA, Nov. 27 to Dec. 2, 2005, p. 857, the contents of which are incorporated herein by reference.

Figure 16:
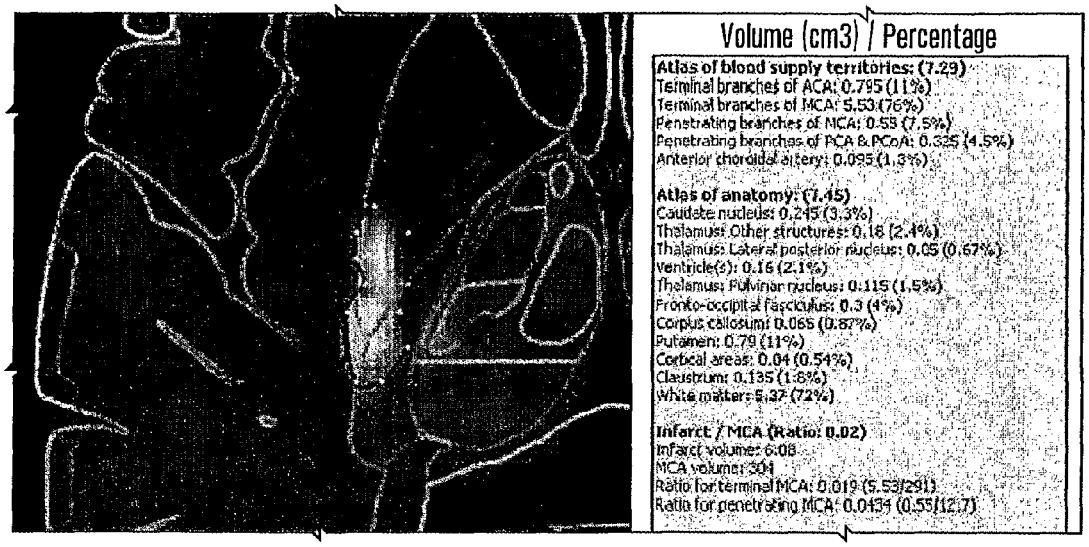
FIGS. 16 and 17 are screenshots showing exemplary superimposed images and quantification data calculated based on the superimposed image.
Figure 17:
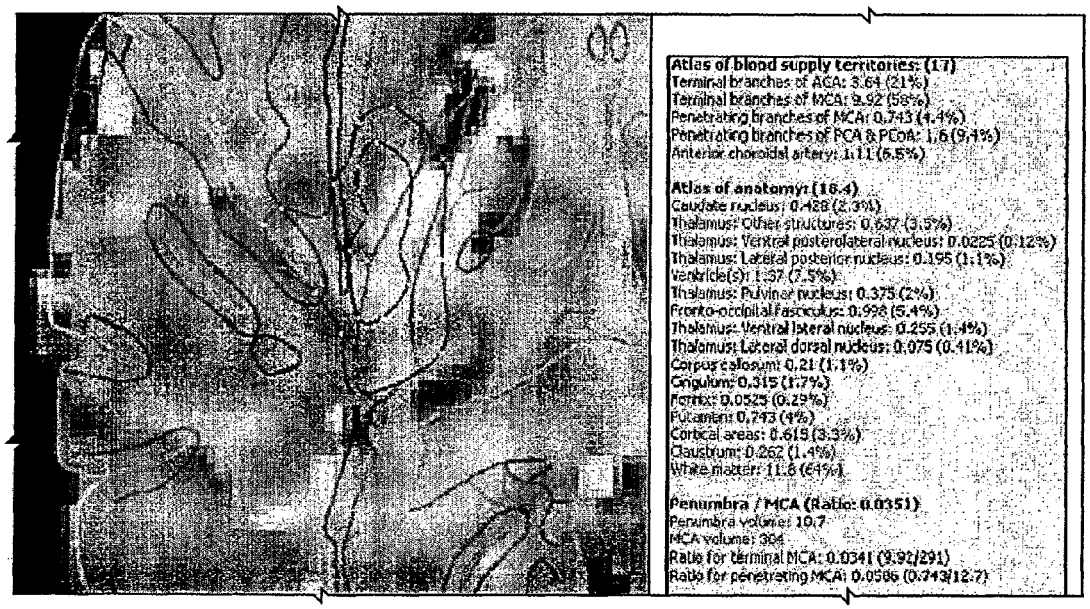

Exemplary superimposed brain images and patient-specific atlas images based on the MSP and BBB technique are shown in FIGS. 16 and 17. FIG. 16 shows a superposition of a diffusion image and the brain atlas images in contour representation, wherein the infarct region is delineated by an infarct contour. FIG. 17 shows a superposition of a perfusion image and the brain atlas images in contour representation, wherein the penumbra region is delineated by a penumbra contour and the infarct contour is also shown. In each case, the names of the specific brain structures that overlap with the actual infarct or penumbra regions are listed in the right-hand panel of the GUI. The volume and percentage of occupancy of each anatomical structure and territory are displayed. In addition, the ratios of infarct to MCA territory and penumbra to MCA territory are also calculated and displayed.

As can be appreciated, the transparency of each displayed image in the superposition may be selected and adjusted to provide improved or different views.

At S314 of FIG. 3, the patient-specific brain atlas images are superimposed with the brain images. The brain atlas images include an anatomy atlas image and a BST atlas image. Contours for delineating the infarct and penumbra regions are also superimposed with the brain images and brain atlas images. The superimposed image may be displayed for visual inspection by a user. The superimposed images may also be automatically processed, such as by computer 100.

Figure 18:
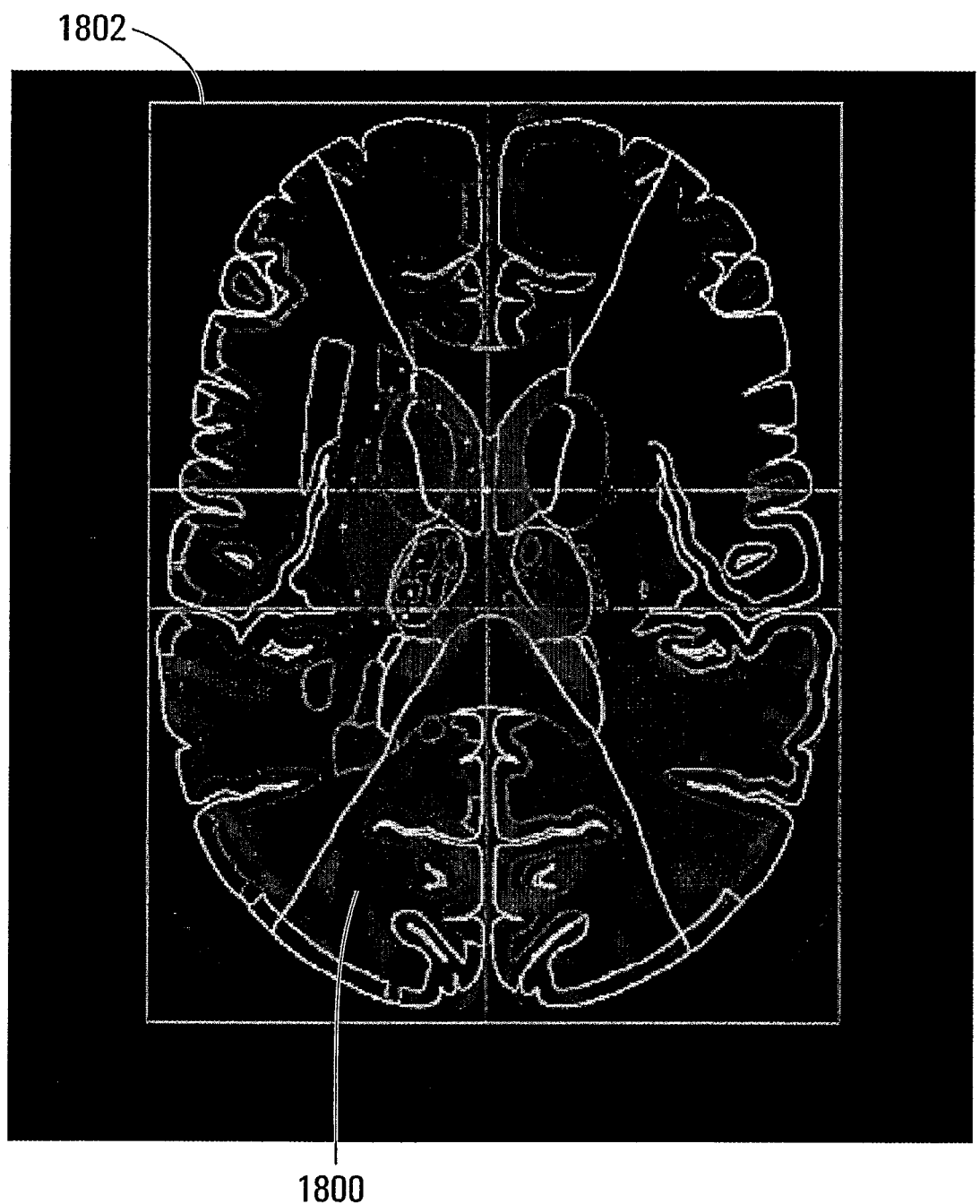
FIG. 18 is an exemplary superimposed image including brain images and brain atlases.

FIG. 18 shows an exemplary superposition 1800 of brain images and patient-specific brain atlas images. Superposition 1800 includes a DWI brain image and a T1-weighted brain image, contours for delineating the infarct and penumbra regions, and atlas images that depict the anatomy structures and BST. The atlas images are displayed in contour representation. The grid lines 1802 show the Talairach grid, which may be moved to interactively warp the atlas images to improve the fit between the atlas/map images and the brain images. As can be seen, the contours and atlas images do not completely block the scanned brain images and the borders of the anatomical structures and BST are visibly marked.

To enhance viewing, different images may be shown in different colors and shades. Different delineated regions and depicted structures may also be shown with different types of contour lines, hatch lines, surfaces, or the like.

At S316 of FIG. 3, the superposition may be optionally further processed and analyzed, either automatically or by a user.

For example, as discussed above, the CAD application 208 may provide a function to automatically calculate the infarct and penumbra volume and the percentage of occupancy for each anatomy structure and blood supply territory.

The relative size, such as volume, of the infarct regions as compared to the MCA territory and the diffusion-perfusion mismatch may be calculated. For example, the volume of infarct and penumbra may be calculated based on the determined infarct and penumbra regions. The volume of the MCA may be calculated from patient-specific atlas images. The BST atlas image may depict the MCA territory. A ratio of the volume of the infarct region and the volume of an overlap between the infarct region and the MCA territory may also be calculated. A volume ratio between the infarct region and the MCA territory may be calculated based on the superimposed images. As can be understood, this information may be used to support the thrombolysis algorithm described in M. W. Parsons et al., "Therapeutic impact of MRI in acute stroke," in *Magnetic Resonance Imaging in Ischemic Stroke*, R. von Kummer and T. Back eds., Springer, Berlin, 2006, pp. 23 to 40, the contents of which are incorporated herein by reference.

To assist stroke diagnosis, the volumes of the actual infarct and penumbra regions may also be calculated or otherwise determined.

The brain images and atlas images may be separated into left and right hemispheres for atlas-to-data mapping.

For each infarct or penumbra region, all of the overlapping anatomical structures or blood supply territories may be identified. If a structure or territory is only partially within the infarct or penumbra region, a ratio of the overlapped portion to the total volume may be calculated and presented to the user. As can be understood by persons skilled in the art, the diffusion-perfusion mismatch may be readily quantified by a semi-automatic extraction of the infarct and penumbra data. For example, the ratio of the volumes of the penumbra to infarct may be calculated based on the delineated infarct and penumbra regions.

The displayed superposition may also be adjusted in various aspects such as viewing angles and zoom factors. Any particular image may be interactively or dynamically modified, such as discussed above. For example, a particular image may be removed or added during inspection if needed. Certain combination of images may be displayed based on information provided and displayed. To focus on different aspects of image analysis, the transparency, color or shading (such as in 3D) of a particular image may be varied. Certain map or atlas images may be re-generated based on current information. For example, segmentation of a particular image may be re-performed or improved based the displayed superposition.

The results of calculation based on the superimposed image may be recorded such as on a computer readable medium for future use, or displayed along with the superimposed image for convenient viewing.

At S318, the final superimposed image may be displayed and the user may inspect the displayed superposition and review any accompanying information to perform stroke diagnosis.

As any overlap between the infarct and penumbra regions and the brain structures are visualized, and the brain structures within the overlap region have been identified, stroke diagnosis may be made quickly and accurately. The superimposed images allow the user to check which anatomical structures and BST are at least partially within the infarct or penumbra.

As the volume ratio between the infarct regions and the MCA territory can be calculated quickly and automatically based on the superimposed brain images and the BST atlas image, the user may be able to make certain diagnostic decisions with increased ease and flexibility. For example, this volume ratio may be used to predict hemorrhagic transformation. The superposition as described herein may also be useful for studying more complicated infarct-BST relationship.

Certain conditions that are not amenable to automatic calculation may be determined by visual inspection. For example, any site of blood vessel occlusion may be identified by visual inspection, in either 2D or 3D representation. In this regard, a 3D vascular model or vascular tree may be generated based on an MRA image, as can be understood by persons skilled in the art. For example, the MRA image may be segmented to produce a 3D geometric model as the vascular model.

Displaying and manipulating the images in 3D, either superimposed or not superimposed, may be advantageous in some applications. For example, the display and manipulation of the infarct and penumbra regions in 3D with user-controlled transparency may increase the accuracy of segmentation of the regions.

In the exemplary embodiments described herein, the captured brain images may be processed quickly and a superimposed image may be generated in a short period of time for timely stroke diagnosis. Test results show that in an exemplary embodiment, the most time consuming process is the FTT of the pre-existing brain atlases, which can be completed within about 5 seconds if no interactive editing of infarct and penumbra contours is performed.

As can be appreciated and discussed above, the superposition of images as described herein can also facilitate quantification of certain aspects or features of the images.

Other features, benefits and advantages of the embodiments described herein not expressly mentioned above can be understood from this description and the drawings by those skilled in the art.

The contents of each reference cited above are hereby incorporated herein by reference.

Of course, the above described embodiments are intended to be illustrative only and in no way limiting. The described embodiments are susceptible to many modifications of form, arrangement of parts, details and order of operation. The invention, rather, is intended to encompass all such modification within its scope, as defined by the claims.

What is claimed is:

1. A method of analyzing brain images of a patient for stroke diagnosis of said patient, comprising:
    capturing a first image of the brain of said patient suitable for determining infarct regions of said brain;
    capturing a second image of said brain suitable for determining penumbra regions of said brain;
    determining an infarct region of said brain from said first image;
    determining a penumbra region of said brain from said second image;
    co-registering said first and second images to a co-ordinate system;
    mapping pre-existing brain atlas images to said co-ordinate system to form patient-specific brain atlas images;
    delineating said infarct region and said penumbra region of said brain on said patient-specific brain atlas images in said co-ordinate system; and
    superimposing said first and second images, with said patient-specific brain atlas images.

2. The method of claim 1, comprising modifying delineation of said infarct region and said penumbra region on said superimposed images.

3. The method of claim 1, comprising determining a degree of overlap between one of said infarct and penumbra regions and a brain structure depicted in said patient-specific brain atlas images.

4. The method of claim 3, wherein said determining a degree of overlap comprises calculating a volume of said overlap.

5. The method of claim 4, wherein said determining a degree of overlap comprises calculating a volume ratio between said volume of said overlap and a volume of said brain structure.

6. The method of claim 5, comprising presenting an identification of said brain structure and at least one of said volume of said overlap and said volume ratio to a user.

7. The method of claim 1, comprising identifying brain structures in said patient-specific brain atlas images that overlap with said one of said infarct and penumbra regions.

8. The method of claim 1, wherein said pre-existing brain atlas images comprise an anatomy atlas image depicting at least one anatomical structure and a blood supply territory (BST) atlas image depicting blood supply territories.

9. The method of claim 8, wherein said BST atlas image depicts a middle cerebral artery (MCA), said method comprising calculating a volume ratio between said infarct region and said MCA.

10. The method of claim 8, wherein said BST atlas image depicts a middle cerebral artery (MCA), said method comprising calculating a volume ratio between said infarct region and an overlap between said infarct region and said MCA.

11. The method of claim 1, wherein said first image comprises a diffusion image.

12. The method of claim 11, wherein said diffusion image is a diffusion weighted imaging (DWI) image.

13. The method of claim 1, wherein said determining said infarct region comprises:
    generating an apparent diffusion coefficient (ADC) map image from at least two diffusion images;
    determining a present infarct region from one of said diffusion images;
    determining a prior infarct region from said one of said diffusion images and said ADC map image; and
    combining said present and prior infarct regions to form said infarct region.

14. The method of claim 1, wherein said second image comprises a perfusion image.

15. The method of claim 14, wherein said perfusion image is a perfusion-weighted imaging (PWI) image.

16. The method of claim 14, wherein said determining said penumbra region comprises:
    generating at least one perfusion map image from said perfusion image, said at least one perfusion map image selected from mean transit time (MTT), cerebral blood flow (CBF), cerebral blood volume (CBV), time to peak (TTP), and peak-height (PKHT) map images;
    superimposing said perfusion image and said at least one perfusion map image; and
    determining an apparent penumbra region from said superimposed perfusion image and said at least one perfusion map image.

17. The method of claim 16, wherein said determining said penumbra region comprises excluding from said apparent penumbra region any overlap with said infract region to form said penumbra region.

18. The method of claim 1, comprising capturing at least one additional image of said brain and superimposing said at least one additional image with said first and second images and said patient-specific brain atlas images, said at least one additional image selected from gradient echo (GRE), fast spin echo (FSE), magnetic resonance angiography (MRA), diffusion weighted imaging (DWI), perfusion weighted imaging (PWI), and fluid-attenuated inversion-recovery (FLAIR) images.

19. The method of claim 1, wherein at least one of said first and second images is a computerized tomography (CT) image.

20. The method of claim 1, wherein each one of said images is two-dimensional (2D) or three-dimensional (3D).

21. A computer readable medium storing computer executable instructions which, when executed by a computer, adopt said computer to perform the method of claim 1.

22. A computer comprising a processor and a computer readable medium, said computer readable medium storing computer executable instructions which, when executed by said processor, adopt said computer to perform the method of claim 1.

23. The computer of claim 22, comprising a display for displaying said images.

* * * * *

UNITED STATES PATENT AND TRADEMARK OFFICE
CERTIFICATE OF CORRECTION

| | | |
|---|---|---|
| PATENT NO. | : 8,019,142 B2 | Page 1 of 1 |
| APPLICATION NO. | : 12/067894 | |
| DATED | : September 13, 2011 | |
| INVENTOR(S) | : Wieslaw L. Nowinski et al. | |

It is certified that error appears in the above-identified patent and that said Letters Patent is hereby corrected as shown below:

On the title page, item (74), in Attorney, Agent, or Firm, in column 2, line 2, delete "Sockton LLP" and insert -- Stockton LLP --

Signed and Sealed this
Eighth Day of November, 2011

David J. Kappos
*Director of the United States Patent and Trademark Office*